US00PP09474P

United States Patent [19]

Dahlqvist-Olsson

[11] Patent Number: Plant 9,474

[45] Date of Patent: Mar. 12, 1996

[54] POINSETTIA PLANT NAMED 'NOBELSTAR'

[75] Inventor: Eva Dahlqvist-Olsson, Malmoe, Sweden

[73] Assignee: Florfis AG, Binningen, Sweden

[21] Appl. No.: 358,881

[22] Filed: Dec. 19, 1994

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of poinsettia plant named Nobelstar, characterized by the combined traits of light coral red bract color, compact and well branched plant habit, medium green foliage, broad elliptically shaped bracts, and medium early flowering repsonse.

1 Drawing Sheet

The present invention relates to a new and distinct cultivar of poinsettia plant, botanically known as *Euphorbia pulcherrima*, and known by the cultivar name Nobelstar.

The new cultivar Nobelstar is a naturally occurring spontaneous mutation of Peterstar, disclosed in U.S. Plant Pat. No. 8,259, characterized by its bright red bract color, medium green foliage, comparatively compact plant habit, medium early response in autumn, and good branching ability.

The new cultivar was discovered by the inventor Eva Dahlqvist-Olsson as a mutation among a group of stock plants of the parent cultivar Peterstar growing in a greenhouse in Malmoe, Sweden in Autumn 1992. One branch of the plant displayed bracts having a substantially lighter, coral red color compared to the bright red bract color of the parent. Shoots developing from the mutated branch were severed by the inventor, planted as cuttings, and grown out. Plants grown our were asexually propagated by the inventor in Malmoe, Sweden in order to obtain a clone with stable and uniform characteristics. Successive generations of asexually reproduced clones were observed to be stable and to relaibly express the distinguishing characteristics of the initially discovered sport.

The following traits have been repeatedly observed and are determined to be basic characteristics of Nobelstar which in combination distinguish this poinsettia as a new and distinct cultivar:

1. Light coral red bract color.
2. Compact and well branched plant habit.
3. Medium green foliage.
4. Medium early flowering response.
5. Broad, elliptically shaped bracts.

Nobelstar has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commerical practice.

Of the many commercial cultivars known to the inventor, the most similar in comparison to Nobelstar is the parent cultivar Peterstar. Nobelstar has a light coral red bract color compared to the bright red bract color of Peterstar, and Nobelstar has displayed a somewhat more compact growth habit, reaching a typical plant height of 22 cm, compared to 25 cm of Peterstar, when plants are grown under the same conditions. Nobelstar can also be compared to the cultivar Fisbon, disclosed in pending application Ser. No. 08/327,929. Both cultivars have similar growth habit and plant height. The bract colors are distinctly different, with Nobelstar having a unique bright light red broad color and Fisbon a more orange-red bract color. In addition, the leaf petioles of Nobelstar are higher than in Fisbon due to less intense anthocyanin coloring, and the reddish color of the styles and top part of the cyathia are lighter in Nobelstar than in Fisbon.

The accompanying color photographic drawing shows typical inflorescence and foliage of a potted plant of Nobelstar, with colors being as true as possible with illustrations of this type.

In the following description, color references are made to The Royal Horticultural Society Colour Chart. The color values were determined indoors in Hillscheid, Germany (latitude 50° N). They were planted as rooted cuttings into 14 cm pots in early June, potted in late June and pinched 14 days later. Plants were grown under dark cloth (short day treatment) from July 25. These plants and those of the comparison cultivar Peterstar were treated with growth regulator Cyocel three times. The last treatment was six weeks before the observation date. Observations and measurements were taken at the beginning of flowering in mid-September.

Classification:

*Botanical.*—*Euphorbia pulcherrima.*

*Commerical.*—Poinsettia, cv. Nobelstar.

Parentage: A naturally occurring mutation from the cultivar Peterstar.

Plant description:

*Form.*—Broad, bushy, 6–7 branches.

*Growth habit.*—Compact growth habit; height approximately 22 cm.

*Rooting.*—Fast; less than 20 days.

*Blooming season.*—From late November (about 9 weeks of response time).

*Blooming habit.*—Saleable from late November, when 3–6 bracts are completely colored.

*Foliage.*—Size: Leaf is approximately 13 cm in length; petiole is 6–7 cm in length. Internodes: 15–20 mm. Color: Mature foliage: Upper surface 137A; under surface 137C. Leaf petiole: Light red. Shape: Elliptical with weak lobes, rounded base. Texture: Upper side, slightly rugose; lower side, weak veins. Edge of margin: Entire. Disease resistance: No unusual susceptibilities to common poinsettia diseases have been noted to date.

Flowering description:

*Cyathias.*—Borne: In a narrow cluster. Quantity: 14–14. Retention: Good.

*Bracts.*—Elliptical, folded along the midrib, surface rugose; largest colored bract with petiole is 16 cm long.

*Color.*—Upper surface 44C; lower surface 46D. By comparison the upper surface bract color of Peterstar is bright red 45B.

Reproductive organs:

*Glands, nectar cups.*—Orange-yellow.

*Stamens.*—Light red turning to brown, hardly any fertile stamens.

*Pollen.*—Very little, yellow in color.

*Styles.*—Light red, 6-lobed stigma.

*Ovaries.*—Triangular, 3-celled, 3 ovules.

I claim:

1. A new and distinct poinsettia plant named Nobelstar, as illustrated and described.

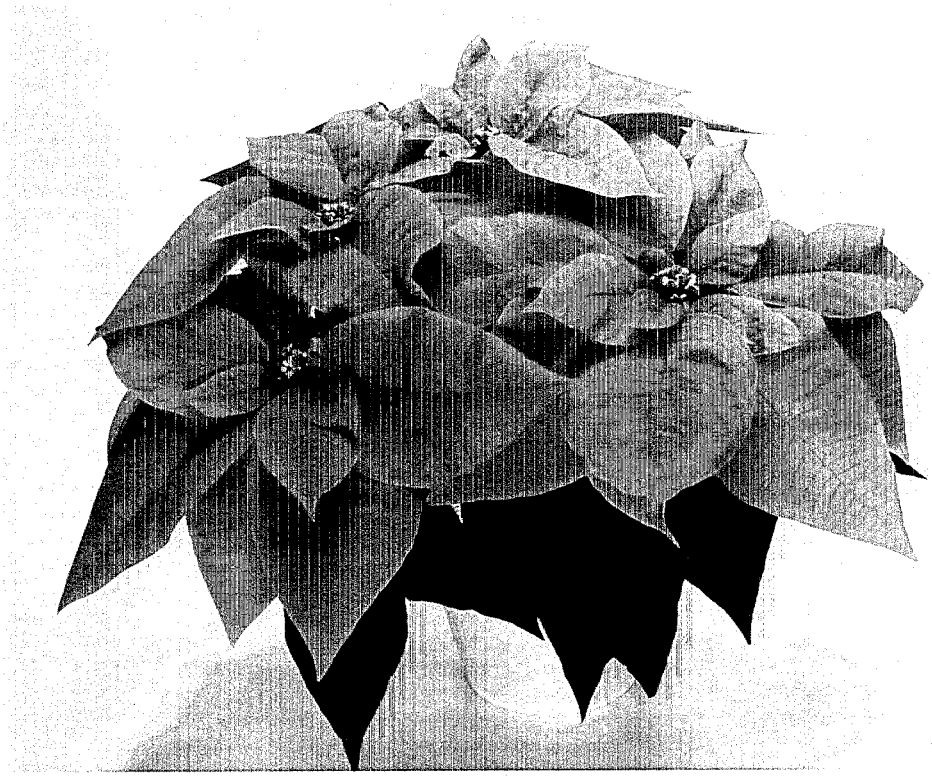

* * * * *